United States Patent
Bailey et al.

[11] Patent Number: 6,120,513
[45] Date of Patent: Sep. 19, 2000

[54] LAPAROSCOPIC SURGERY INSTRUMENTATION AND METHOD OF ITS USE

[76] Inventors: Robert W. Bailey, 516 S. Sydbury La., Wynnewood, Pa. 19096; Giles H. Manley, 13 Wetherbee Ct., Phoenix, Md. 21131

[21] Appl. No.: 09/004,988

[22] Filed: Jan. 9, 1998

[51] Int. Cl.[7] .................................................. A61B 17/04
[52] U.S. Cl. .......................................... 606/141; 606/139
[58] Field of Search ........................... 128/831; 606/139, 606/140, 141, 148, 113, 144

[56] References Cited

U.S. PATENT DOCUMENTS

| | | | |
|---|---|---|---|
| 529,936 | 11/1894 | McNalley | 606/141 |
| 1,606,497 | 11/1926 | Berger . | |
| 2,087,108 | 7/1937 | Irvine . | |
| 2,115,298 | 4/1938 | Brown | 128/309 |
| 3,739,784 | 6/1973 | Itoh | 128/320 |
| 3,835,859 | 9/1974 | Roberts et al. | 606/140 |
| 3,911,923 | 10/1975 | Yoon | 128/303 A |
| 3,989,049 | 11/1976 | Yoon | 128/326 |
| 4,226,239 | 10/1980 | Polk, et al. | 128/303 A |
| 4,869,268 | 9/1989 | Yoon | 128/831 |
| 5,098,440 | 3/1992 | Hillstead | 606/108 |
| 5,122,147 | 6/1992 | Sewell, Jr. | 606/110 |
| 5,123,906 | 6/1992 | Kelman | 606/107 |
| 5,171,233 | 12/1992 | Amplatz et al. | 606/113 |
| 5,190,554 | 3/1993 | Coddington, III et al. | 606/113 |
| 5,226,908 | 7/1993 | Yoon | 606/141 |
| 5,284,474 | 2/1994 | Adair | 604/164 |
| 5,480,410 | 1/1996 | Cuschieri, et al. | 606/213 |
| 5,522,791 | 6/1996 | Leyva | 600/207 |
| 5,593,416 | 1/1997 | Donahue | 606/170 |
| 5,704,943 | 1/1998 | Yoon et al. | 606/139 |
| 5,766,217 | 6/1998 | Christy | 606/148 |
| 5,908,429 | 6/1999 | Yoon | 606/144 |
| 5,921,993 | 7/1999 | Yoon | 606/140 |

*Primary Examiner*—Gary Jackson
*Attorney, Agent, or Firm*—Robert S. Lipton, Esq.; Lipton, Weinberger & Husick

[57] ABSTRACT

An operative laparoscopic instrument is equipped with proximal and distal loops closed by slip knots and tightenable from the proximal end of the instrument. A forceps extending from the distal end of the instrument grasps an anatomical tube to be both ligated and transected and pulls it into the instrument past both loops. The distal loop is first tightened to ligate the tube and the proximal loop is then tightened to transect the tube.

13 Claims, 12 Drawing Sheets

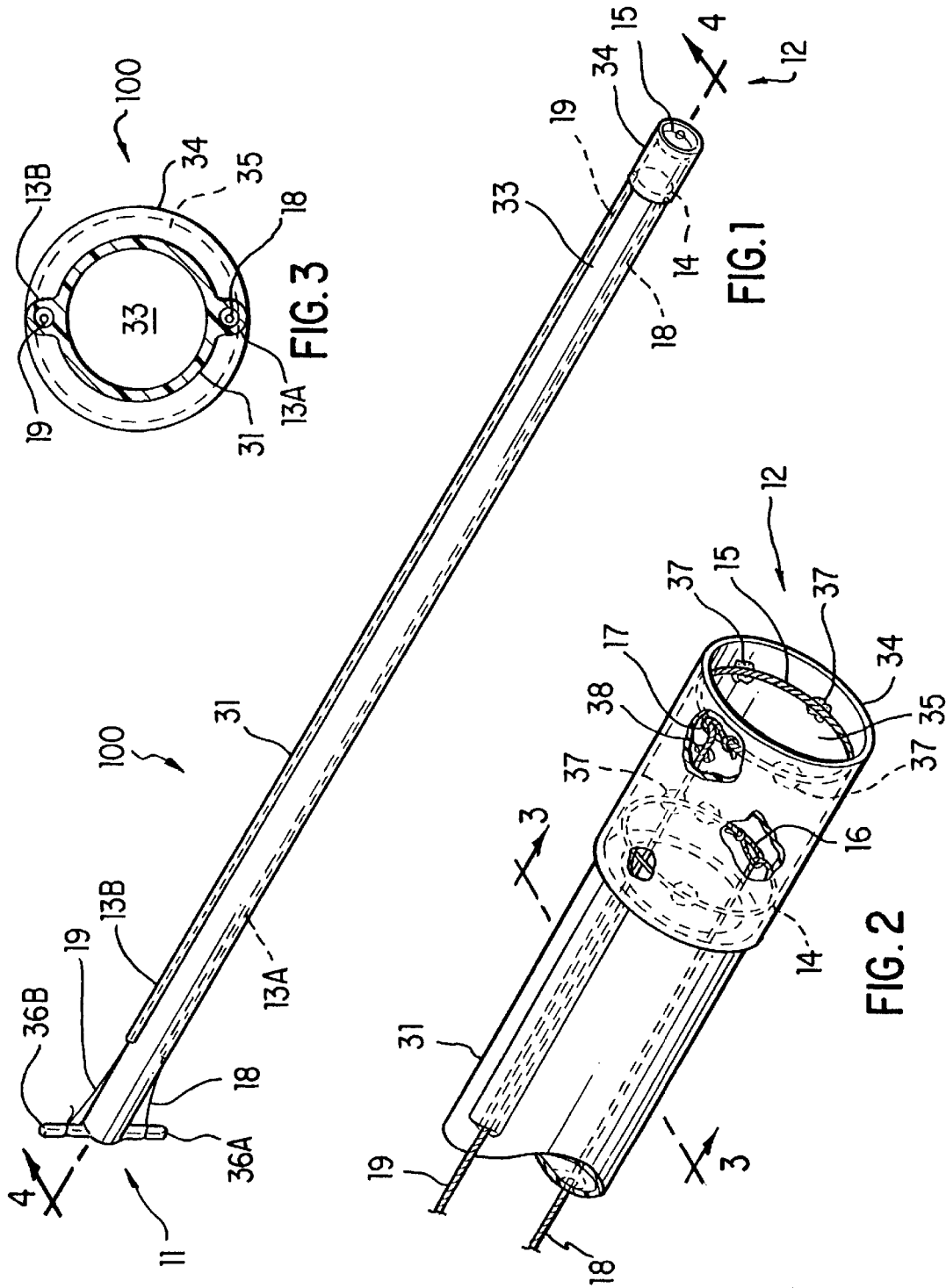

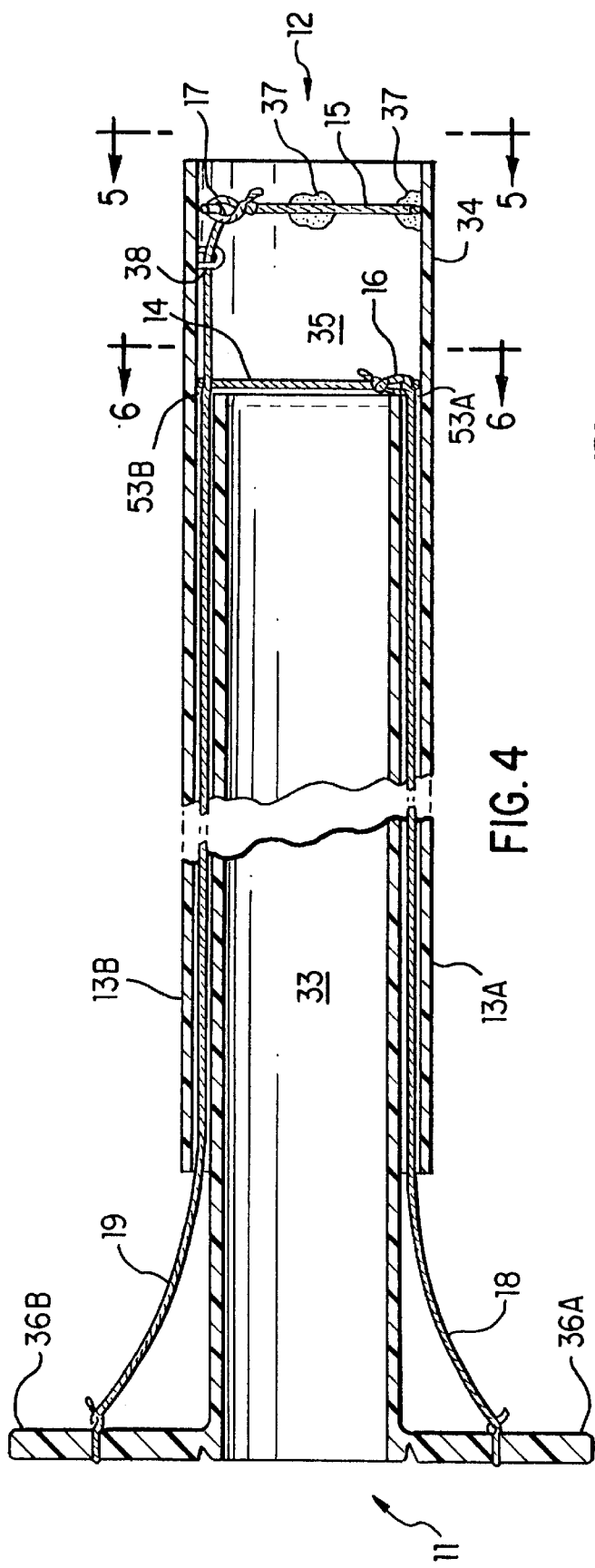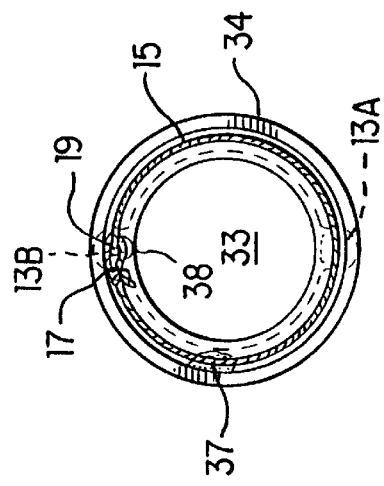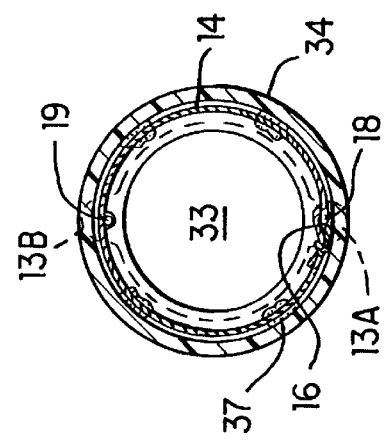

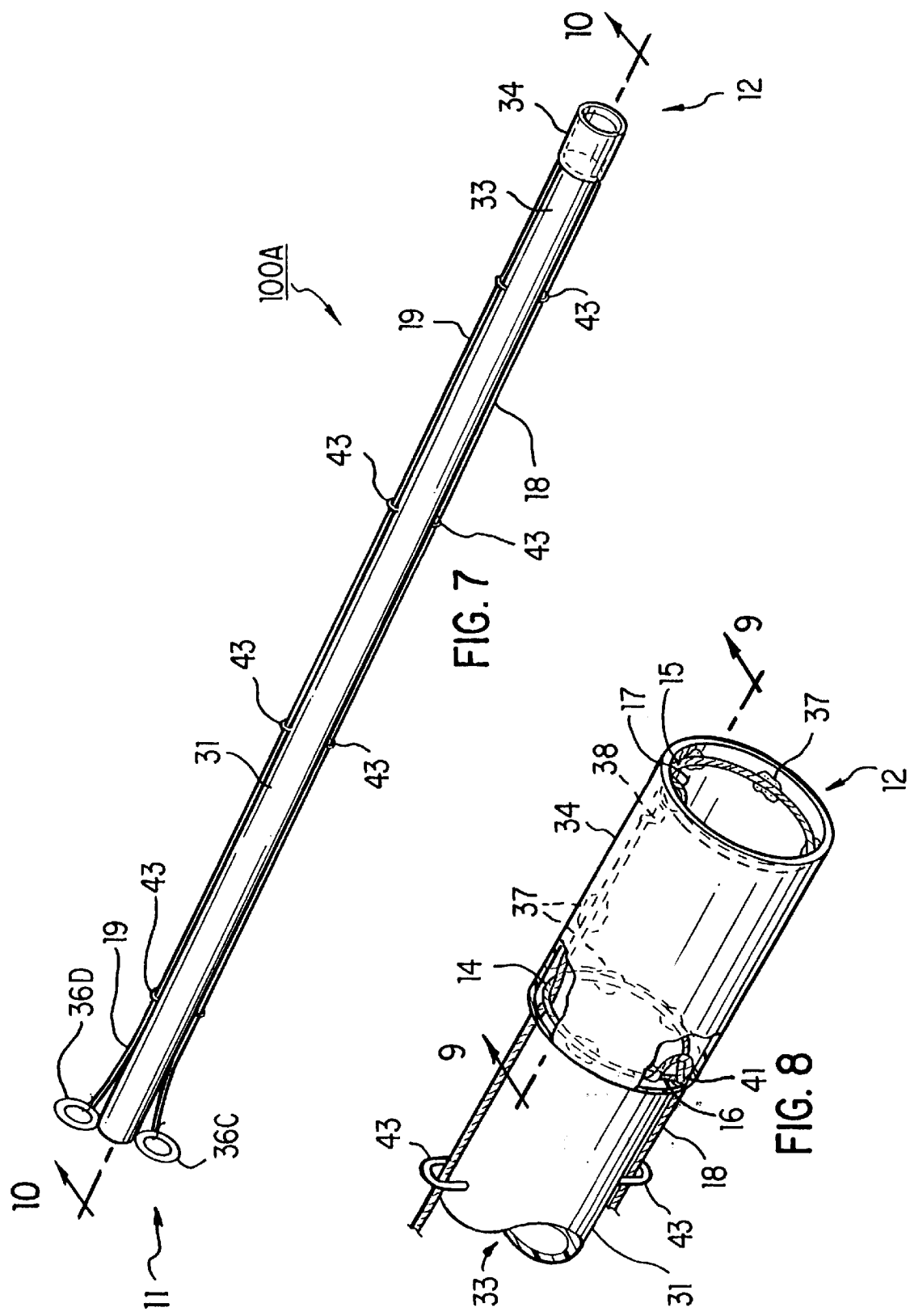

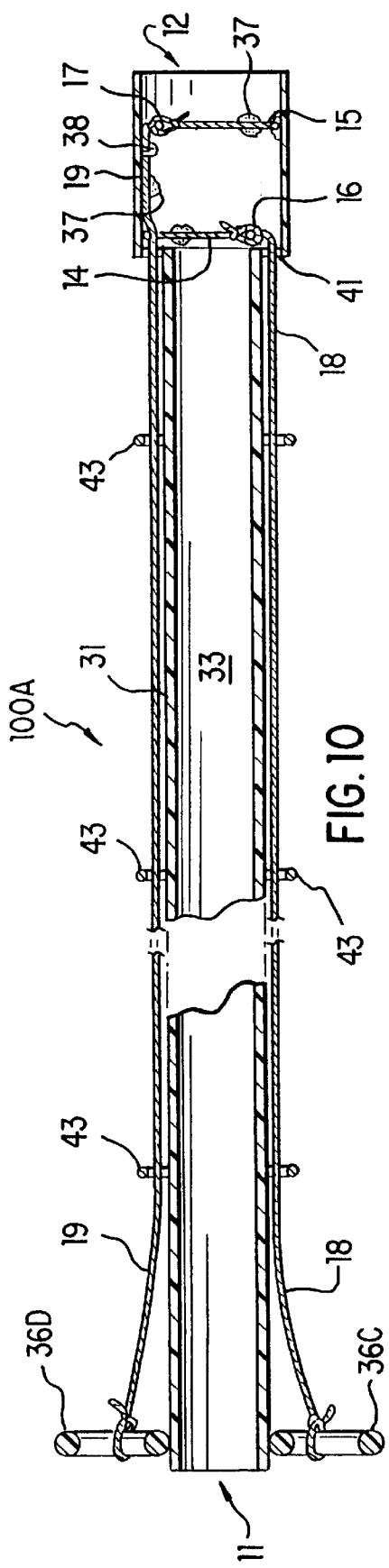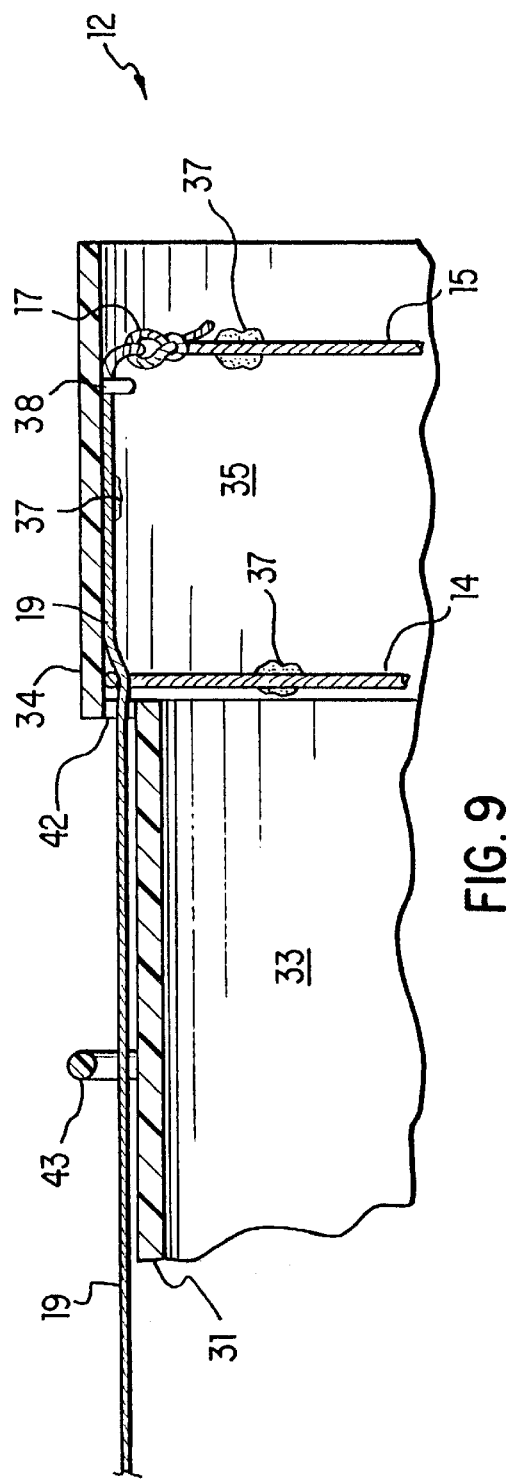

LAPAROSCOPIC SURGERY INSTRUMENTATION AND METHOD OF ITS USE

BACKGROUND OF THE INVENTION

The present invention relates to laparoscopic surgery and more particularly to instrumentation for such surgery and the surgical procedures in which that instrumentation is used.

It is known to use a laparoscope for such surgical procedures as tubal ligation. This could be conducted through a single trocar, utilizing the "instrument channel" of an operating laparoscope. Thus, the entire laparoscopic procedure could be performed through a single incision, namely that through which the laparoscope is inserted.

This known instrumentation and the procedures for its use have had some serious drawbacks. For example, in performing tubal ligation, there was no opportunity to simultaneously remove a segment of the Fallopian tube which was undergoing ligation. Therefore, a pathologic (histologic) evaluation could not be performed and incontrovertible evidence (so-called "tissue confirmation") could not be provided as part of the same procedure that a complete tubal ligation had taken place.

To obtain such a segment, it has been necessary to place one or two additional trocars, which added to the cost, risk and duration of the operative procedure.

Accordingly, it is an object of the present invention to provide surgical instrumentation and procedures for its utilization, which overcome one or more of the drawbacks of the prior art.

It is another object to provide such instrumentation and procedures which are particularly suitable for the performance of tubal ligation.

It is still another object to provide such instrumentation and procedures which yield "tissue confirmation" by means of the same instrument and procedure as the ligation itself.

It is still another object to provide such an instrument and procedure which requires placement of only a single trocar.

BRIEF DESCRIPTION OF THE INVENTION

The foregoing objects and still others which will appear, are achieved in accordance with the present invention as follows.

A laparoscopic instrument is equipped with two so-called "ligating loops." Such loops are known, in themselves, and are currently used to ligate an anatomic structure, such as a blood vessel, bile duct or Fallopian tube. They consist of a pre-tied suture which terminates in a loop closed by a slip knot. The loop is placed around the anatomic structure to be ligated and is tightened around that structure by pulling on the free end of the suture, which protrudes from the patient's body through the outside end of the laparoscopic sheath.

In accordance with the present invention, not one, but two such loops are positioned inside and near the distal end of the laparoscopic instrument, at different locations along the length of the instrument. The loop closest to the proximal end of the instrument will be referred to as the proximal loop and the other as the distal loop.

Also in accordance with the invention, the suture leading from the slip knot of the distal loop is led through the proximal loop on its way to protruding from the proximal end of the laparoscopic instrument.

In use, the laparoscopic instrument is placed with its distal end close to the portion of the anatomic structure at which the ligation is to take place.

A grasping forceps is inserted through the same laparoscopic instrument, so that it passes through both loops and extends beyond the distal end of the laparoscopic instrument, where it grasps the anatomic structure to be ligated. This forceps is then withdrawn far enough into the laparoscopic instrument to pull the grasped structure through and past both ligating loops. The distal loop is then pulled tight, thereby performing the ligation at the loop's location. Thereafter, the proximal loop is pulled tight. This proximal loop is made of a fine (sharp) wire which transects the portion of the anatomic structure that extends through the proximal loop and also cuts the distal suture above its slip knot. Finally, the forceps is used to withdraw the transected portion from the laparoscopic instrument, thereby providing the desired "tissue confirmation". The ligated portion is free to exit from the distal end of the laparoscopic instrument.

BRIEF DESCRIPTION OF THE DRAWINGS

For further details reference is made to the discussion which follows, in light of the accompanying drawings, wherein FIG. 1 is a diagrammatic illustration of an operative laparoscopic instrument embodying the present invention;

FIG. 2 is an enlarged view of the distal end of the laparoscopic instrument shown in FIG. 1;

FIG. 3 is a radial cross-sectional view of the laparoscopic instrument shown in FIG. 2, taken along line 3—3;

FIG. 4 is an axial cross-sectional view of the laparoscopic instrument shown in FIG. 1, taken along line 4—4;

FIG. 5 is a distal end view of the laparoscopic instrument shown in FIG. 4, taken along line 5—5;

FIG. 6 is a radial cross-sectional view of the laparoscopic instrument shown in FIG. 4, taken along line 6—6;

FIG. 7 is a second embodiment of a laparoscopic instrument in accordance with the present invention;

FIG. 8 is an enlarged view of the distal end of the laparoscopic instrument shown in FIG. 7;

FIG. 9 is a partial axial cross-sectional view of the laparoscopic instrument shown in FIG. 8, taken along line 9—9;

FIG. 10 is an axial cross-sectional view of the instrument shown in FIG. 8, taken along line 10—10.

DETAILED DESCRIPTION OF THE INVENTION

Figure 11:
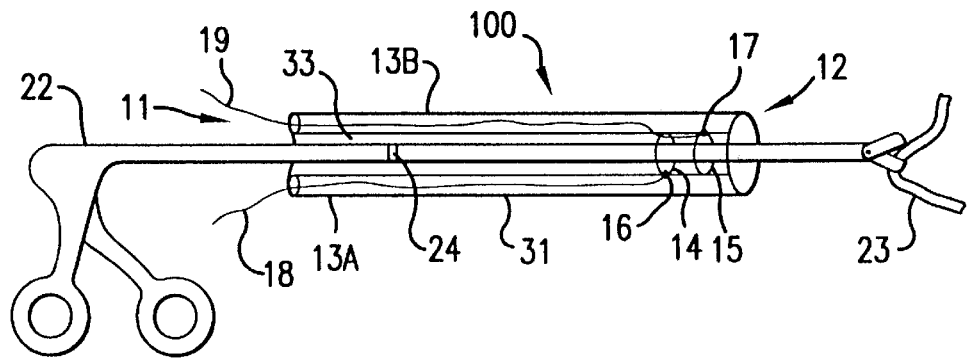
FIG. 11 is a diagrammatic illustration of the instrument shown in FIG. 1, together with a grasping forceps seizing the tube to be ligated.

In describing a preferred embodiment of the invention, specific terminology will be selected for the sake of clarity.

However, the invention is not intended to be limited to the specific terms so selected, and it is to be understood that each specific term includes all technical equivalents that operate in a similar manner to accomplish a similar purpose.

Referring now to FIG. 1, a laparoscopic instrument 100 in accordance with the present invention comprises an elongated cannula 31, having a proximal end 11 and a distal end 12. The cannula 31 is preferably of a tubular shape and is open at both its proximal end 11 and its distal end 12. A primary interior channel 33 extends the entire length of the elongated cannula 31.

Two secondary channels 13A and 13B, located on the exterior surface of cannula 31, run generally parallel to the interior channel 33. Although the secondary channels 13A and 13B can be spaced anywhere on the cannula, they are preferably positioned diametrically opposite to each other. The channels 13A, 13B are primarily used to guide and support sutures 18, 19, respectively.

Referring now to FIG. 2, a distal support tube 34, having an interior passage 35, is attached to the distal end of the elongated cannula 31. The diameter of interior passage 35 is slightly greater than the diameter of the elongated cannula 31 so that channels 13A and 13B open into passage 35 via apertures 53A, 53B, respectively, as shown in FIGS. 2 and 3.

In the preferred embodiment, the exterior surface of the laparoscopic instrument would have a continuous, generally cylindrical shape. This can be done by a variety of manufacturing methods. For example, the distal support tube 34 can be replaced by an exterior sheath (not shown) that runs from a point just short of the proximal end 11 to a point at which the support tube 34 would normally terminate to form distal end 12. The exterior sheath would provide the laparoscopic instrument 100 with a smooth or continuous exterior surface. In another example, two longitudinal holes could be drilled through a relatively thick-walled tube; the two longitudinal holes would form the secondary channels 13A and 13B, and the interior of the tube would form interior channel 33. The continuous exterior surface would facilitate entry and egress from a patient's body.

The dual loop feature will now be described, with reference to FIGS. 2, and 4–6. Two open loops 14 and 15 are positioned inside interior passage 35 of support tube 34. Loop 14 (the proximal loop) is farther from distal end 12 of sheath 100 than loop 15 (the distal loop). Loops 14 and 15 may be closed by a slip knot 16 and 17, respectively.

It is important to note that suture 19 must pass through loop 14 if full advantage of this invention is to be achieved. The reason behind this will become clear during the discussion of the method of this invention which follows.

Loops 14, 15 (and by extension channel 33 and passage 35) must be large enough to allow a medical instrument to pass through their respective interiors as illustrated below. If necessary, a non-toxic adhesive 37, or dissolvable tape, may be used to secure both loops 14, 15 (and, if necessary, a portion of sutures 18 and 19) to the interior surface of support tube 34.

Suture 18 cooperates with slip knot 16 for closing proximal loop 14. Similarly, suture 19 cooperates with slip knot 17 for closing distal loop 15. Sutures 18 and 19 are threaded through their respective secondary channels 13A, 13B, and are long enough so that their "free" ends protrude from the proximal end of its respective secondary channel.

When either suture 18 or 19 is retracted from its respective channel 13A or 13B, the diameter of the loop 14 or 15 will decrease when the slip knot 16 or 17 engages a stationary object. In one embodiment, the diameter of the aperture 53A of channel 13A is smaller than slip knot 16 to prevent its passage there through. Therefore, as suture 18 is retracted, slip knot 16 engages an interior portion of support 34 and loop 14 closes.

A U-shaped stop 38 is preferably provided on the interior surface of support tube 34. As suture 19 is retracted, slip knot 17 engages stop 38 and closes loop 15. Alternatively, a portion of slip knot 17 may be secured to the inner surface of tube 34 using non-toxic glue in a manner such that the glue does not interfere with the operation of the slip knot 17.

In the preferred embodiment, the elongated cannula 31 is manufactured from plastic along with channels 13A, 13B, and distal support tube 34. Loops 14, 15 and sutures 18, 19 are placed in their proper position before sealing the entire laparoscopic instrument 100 in a sterile package.

The "free" ends of sutures 18 and 19 may be left dangling at the proximal end of the sheath 100. However, FIGS. 1 and 4 illustrate means for securing the free ends of the sutures so that they can be quickly located and grasped. Breakaway rods 36A, 36B project from the outer surface of elongated cannula 31 substantially at the proximal end. The free ends of sutures 18, 19 are secured or tied to breakaway rods 36A, 36B, respectively. When it is time to close the loops 14, 15, the breakaway rods 36A, 36B are bent back-and-forth until they break off from the elongated cannula 31. By pulling on the detached breakaway rods, sutures 18, 19 are extracted from their respective channels 13A, 13B.

Referring now to FIGS. 7 and 8, a second embodiment is illustrated. Instead of secondary channels 13A, 13B, a plurality of U-shaped loops 43 protrude from the outer surface of elongated cannula 31 to keep sutures 18, 19 in place. In order to present a smooth exterior surface, the cannula 31 can be inserted into tubularly-shaped sheath (not shown).

As shown in FIGS. 8 and 9, distal support tube 34 includes apertures 41, 42 to allow entry of sutures 18, 19, respectively. In the preferred embodiment, aperture 41 is smaller than slip knot 16 to close loop 14 when suture 18 is withdrawn. Stop 38 performs the same function as described above for engaging slip knot 17 to close loop 15.

As illustrated in FIGS. 7 and 10, an alternate means of securing the free ends of the sutures is disclosed. Rings 36C and 36D replace rods 36A and 36B, and are temporarily secured to the outer surface of elongated cannula 31 via breakaway tabs. The rings 36C, 36D preferably have a diameter large enough to permit the insertion of a finger therethrough, reducing the possibility of losing track of the free ends of sutures 18, 19, and helping the surgeon's control of the ligation and transection.

FIG. 11, to which reference may now be made, illustrates a method of practicing this invention utilizing the laparoscopic instrument 100 of FIG. 1. An incision is made in the patient and the laparoscopic instrument 100 is inserted through the incision. A grasping forceps 22 is inserted through primary channel 33 and extended beyond the distal end 12 of cannula 31. The forceps 22 grasps the anatomic structure (e.g., Fallopian tube 23) which is to be both ligated and transected. The forceps 22 must pass through both loops 14, 15 as illustrated.

Figure 12:
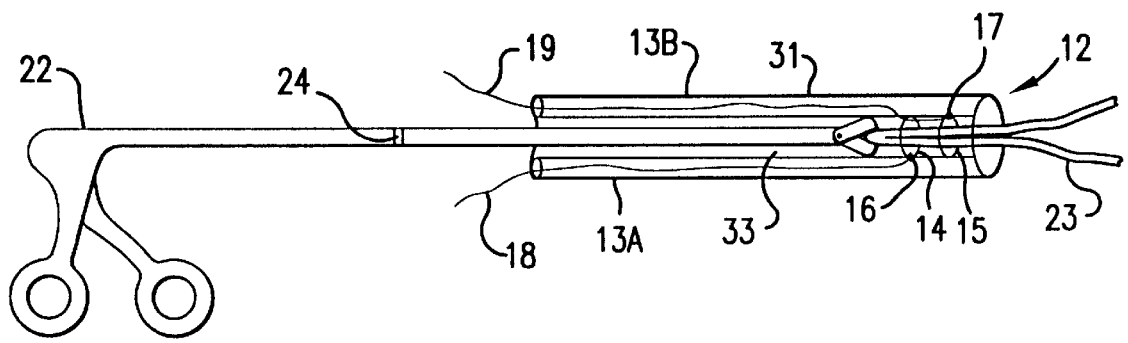
FIG. 12 is a diagrammatic illustration of the instrument shown in FIG. 11, but now with the tube to be ligated pulled inside the cannula in accordance with the invention.

FIG. 12 shows forceps 22 retracted into primary channel 33 and back through loops 14, 15 until it has drawn the grasped portion of Fallopian tube 23 well into the primary channel 33. In so doing, the Fallopian tube 23 becomes folded over, as illustrated in FIG. 12, and this folded portion is positioned inside of both loops 14 and 15.

Figure 13:
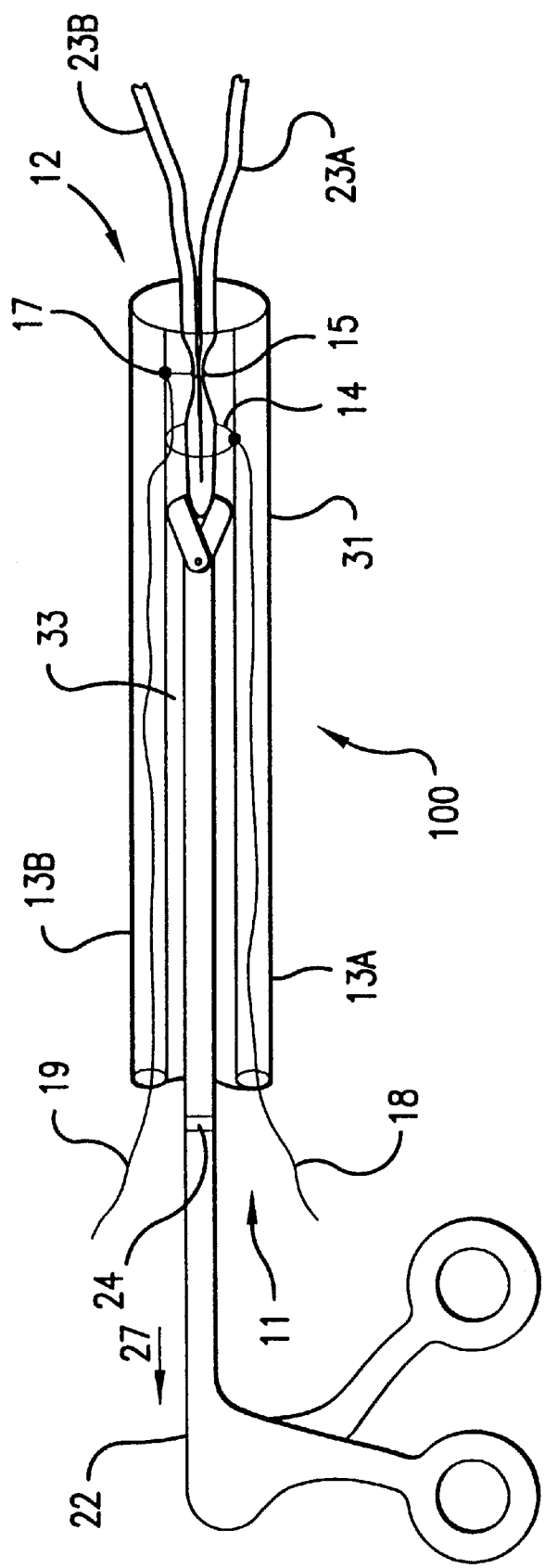
FIG. 13 is a diagrammatic illustration of the same instrument as in FIGS. 11 and 12, after ligation has been performed, but before transection.

For convenience in determining how far to retract forceps 22 for the above-described purpose, the shaft of the forceps 22 may be provided with a visual mark 24 as shown in FIGS. 11, 12 and 13. When that mark 24 emerges from the proximal end of primary channel 33 of cannula 31, the forceps 22 will have been sufficiently retracted within the cannula 31 to clear both loops 14 and 15 which properly positions the Fallopian tube 23.

Referring now to FIG. 13, this shows the effect of performing the next step in the method of the invention. That step involves tightening slip knot 17 thereby closing distal loop 15 around the portion of Fallopian tube 23 which extends through that loop 15 by pulling on the free end of suture 19 in the direction of arrow 27. By so doing, the Fallopian tube becomes ligated at the location of the tightened loop 15. Indeed, this might even be described as a double ligation, since both legs 23A and 23B of tube 23 are, in effect, closed off by the tightened loop 15.

If rods 36A and 36B are utilized, then rod 36B is bent back and forth until it breaks free of the cannula 31. The rods give the surgeon performing the operation greater precision of the ligation and transection by improving control of the extraction of the sutures.

Figure 14:
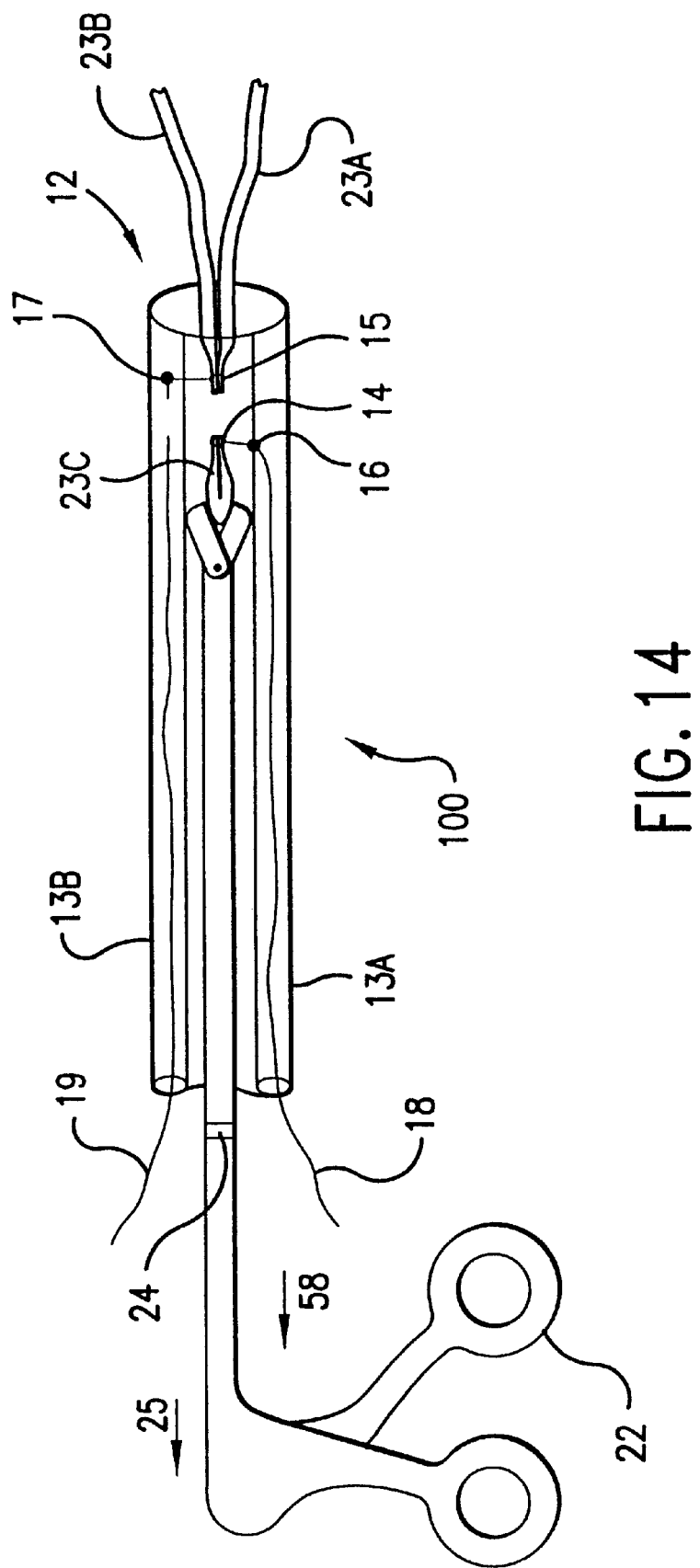
FIGS. 14 and 15 are diagrammatic illustrations of the instrument shown in FIG. 11, after both ligation and transection have been performed.

Referring now to FIG. 14, this shows the effect of performing the next step in practicing the invention. That step involves tightening slip knot 16 that in turn closes proximal loop 14 around the portion of Fallopian tube 23 which extends through that loop 14 by pulling on the free end of suture 18 in the direction of arrow 58. Again, rod 36A or ring 36C improves the surgeon's control of extracting suture 18.

While distal loop 15 is made of conventional material used for ligations, proximal loop 14 is made of a material which, when urged against an anatomic structure such as Fallopian tube 23, will cut through that structure. For example, this material may be a thin wire, strong enough to perform such cutting through the Fallopian tube 23 when pressed against it by the closing of proximal loop 14. As indicated previously, suture 19, which passes through loop 14, is also cut by the process of closing proximal loop 14. This separates suture 19 from slip knot 17 and distal loop 15.

Figure 15:
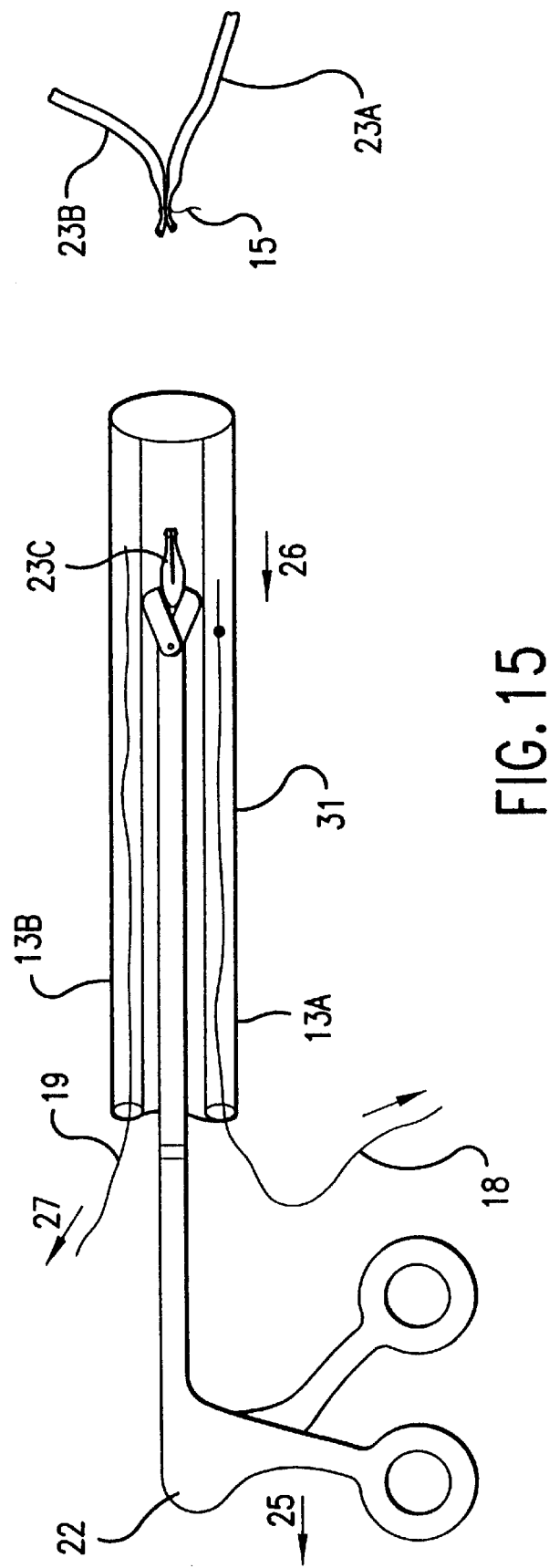

As for distal loop 15, as shown in FIGS. 13–15, this now-closed loop remains with the ligated Fallopian tube. Within a few weeks, the distal loop 15 dissolves. Suture 19 is carried out by pulling on suture 19 in the direction of arrow 27 until it clears proximal end of channel 13B.

After loop 14 cuts through the Fallopian tube as described above, there remains grasped by forceps 22 only the very end portion 23C of the Fallopian tube. This end portion 23C is then withdrawn from the laparoscopic instrument 100 by withdrawing forceps 22 completely from the cannula 31, in the direction indicated by arrow 25 in FIG. 15. The severed portion 23C provides the desired "tissue confirmation" for histologic evaluation. The remainder of Fallopian tube 23A and 23B, having now been severed from end portion 23C, is free to remain in its prior location inside the patient's body, either by moving spontaneously out of the laparoscopic instrument 100, or after instrument 100 is withdrawn in the direction of arrow 26.

The tightened proximal loop 14 is reduced essentially to the size of its slip knot 16 in the course of severing tube portion 23C. This slip knot is then withdrawn, together with its attached suture 18, through withdrawal of laparoscopic instrument 100 from the patient in the direction of arrow 26.

Figure 16:
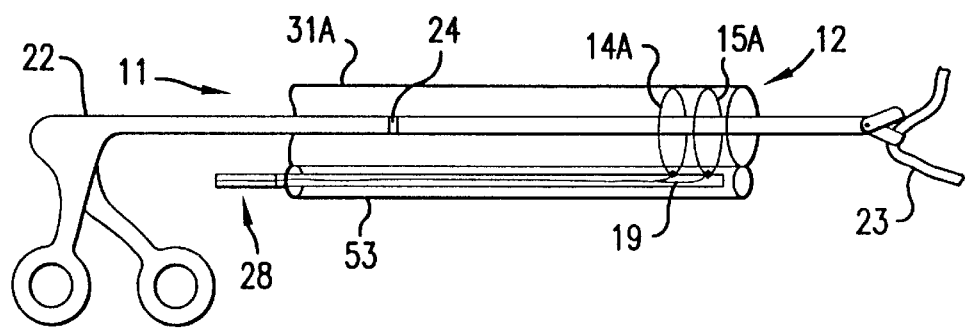
FIG. 16 is a diagrammatic illustration of a third embodiment of a laparoscopic sheath embodying the present invention.

Turning now to FIG. 16, an alternative embodiment of the invention is shown. In this embodiment, cannula 31A includes only a single secondary channel 53. A pusher rod 28 is inserted into secondary channel 53. Although rod 28 is shown with its distal end inside cannula 31A, it may be made longer than cannula 31A so that its distal end projects from the distal end of channel 53.

Pusher rod 28 is similar to single loop rods now in use but is modified to include two loops 14, 15. Pusher rod 28 is relatively rigid. Loops 14 and 15 are attached at the opposite (distal) end of rod 28 so as to be movable in the axial direction when the rod 28 is moved in that same direction. In addition, suture 19 is threaded through the interior of loop 14 for reasons which were explained earlier. The proximal ends of sutures 18, 19 are attached to a breakaway handle 60.

In FIG. 16, the grasping forceps 22 is shown in the same position as in FIG. 11, namely grasping the portion of anatomic structure 23 where the ligation and transection are to take place.

Figure 17:
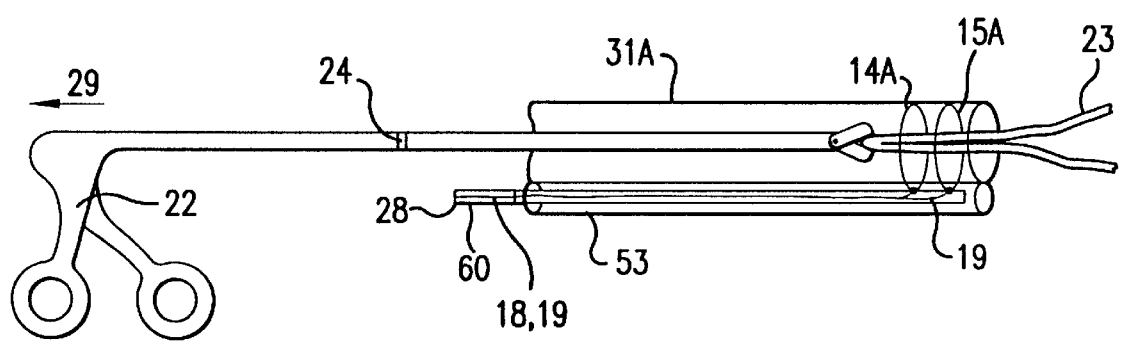
FIGS. 17–20 are diagrammatic illustrations of the same embodiment as in FIG. 16, but at successively later stages in its utilization.

Referring now to FIG. 17, this shows the next stage in the utilization of this alternative embodiment. Grasping forceps 22 are displaced in the direction of arrow 29, carrying Fallopian tube 23 with it, until the forceps 22 has cleared both loops 14, 15 which is generally the equivalent of that shown in FIG. 12.

Figure 18:
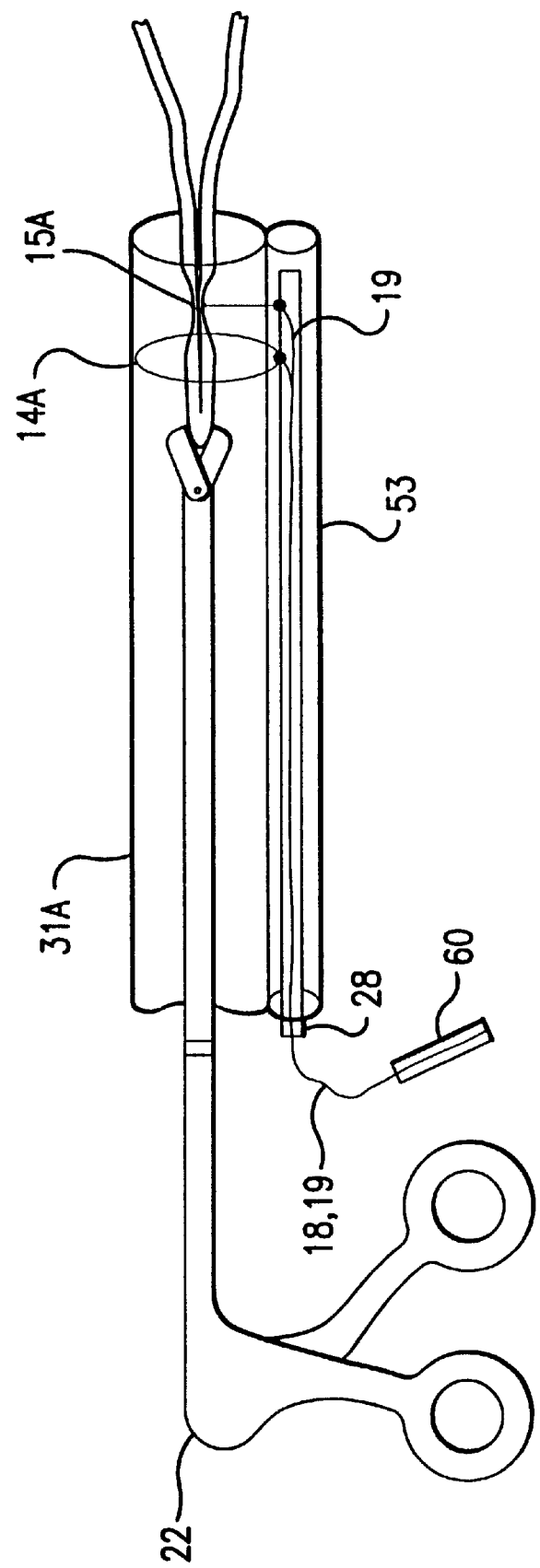

Referring now to FIG. 18, this shows the ensuing ligation of tube 23 by means of this alternative embodiment, through pulling on suture 19, i.e., in the manner equivalent to that which is shown in and described with reference to FIG. 13. By detaching breakaway handle 60 from the rest of the pusher rod 28, the controlled removal of suture 19 can be achieved.

Figure 19:
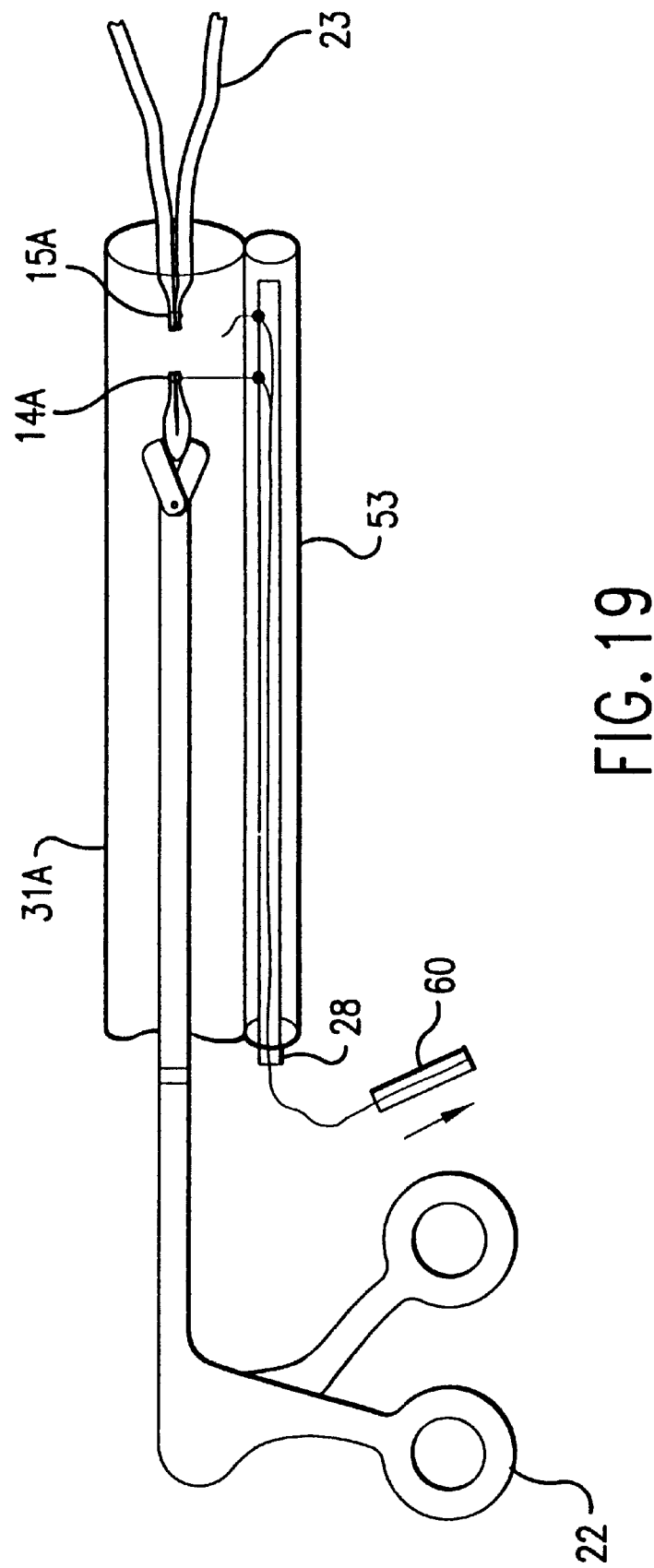

As for FIG. 19, this shows the subsequent transection of tube 23 by means of this alternative embodiment of the invention, through pulling on suture 18 so as to close proximal loop 14 and thereby sever portion 23C of the Fallopian tube 23, as well as simultaneously severing suture 19. In its initial state, suture 19 is relatively taut as compared to suture 18. Therefore, even though suture 18 is also connected to breakaway handle 60, loop 15 closes first until the slack in suture 18 is taken up, thereby tightening loop 14.

Figure 20:
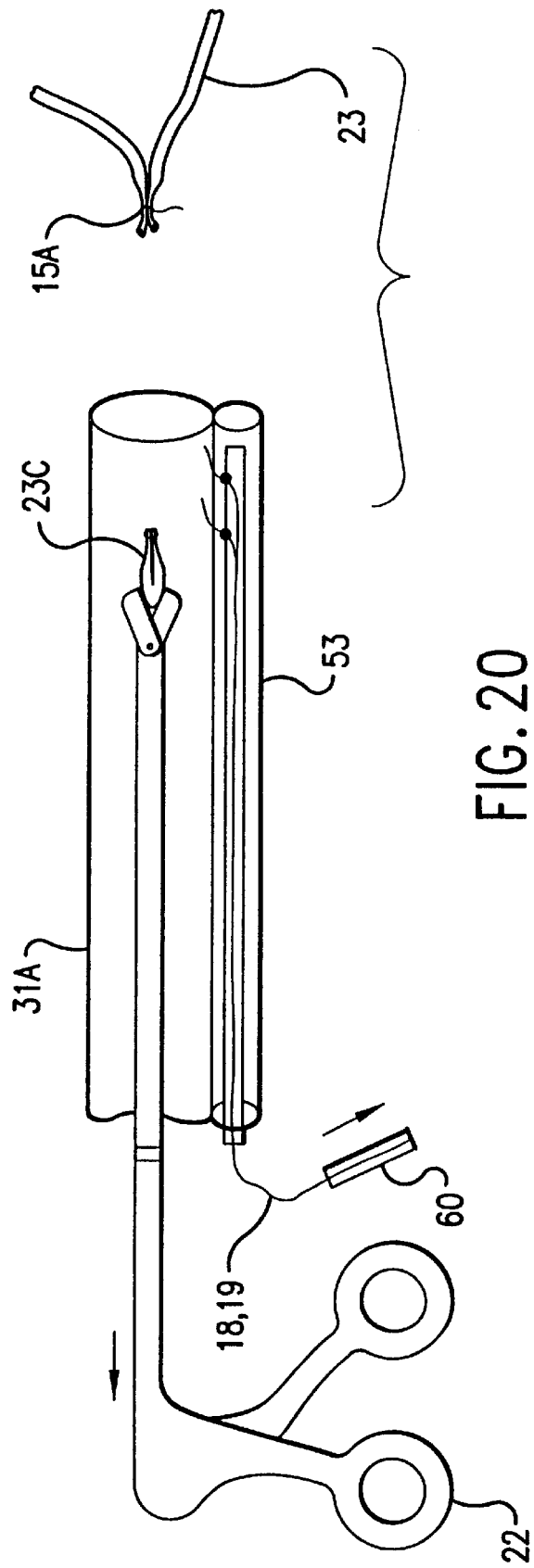

This severed portion 23C is then withdrawn by forceps 22 through cannula 31A, as shown in FIG. 20, while the ligated portion remains inside the patient's body cavity. Rod 28 may be withdrawn before or simultaneously with cannula 31A.

It will be understood that various modifications will occur to those skilled in the art without departing from the inventive concept. For example, the grasping forceps 22 may be incorporated right from the start into the overall instrument, so that it is available for immediate use once the cannula 31 is placed in the patient's body. This would also make it more convenient to provide the mark 24, which denotes the appropriate extent of pull-back of the forceps after it has grasped the Fallopian tube 23.

Likewise, in the embodiment of FIGS. 16 to 20, the pusher rod 28 may be an integral part of the present instrument from the start (i.e., pre-positioned in channel 53). This would make it promptly available when needed and would also insure that it is appropriately proportioned in relation to the other dimensions of the instrument.

Furthermore, the instrument and method of the invention is not limited to use with Fallopian tubes, but can be practiced in any surgical situation in which a comparable anatomic structure is involved. It will be apparent to those skilled in the art that various changes and modifications may be made to the apparatus described herein which clearly fall within the scope of this invention. In view of all this, it is desired to protect the inventive concept broadly within the spirit and scope of the appended claims.

What is claimed is:

1. An instrument for use in laparoscopic surgery, comprising:

a cannula insertable into a patient's body for the performance of said surgery;

a pair of sutures supported by said cannula, each suture terminating in a closable open loop within said cannula near its distal end, one of said loops being positioned closer to said distal end than the other of said loops, the suture from said distal loop passing through said other loop.

2. The instrument of claim 1, wherein said distal loop is made of ligating material, and said other loop is made of transacting material.

3. The instrument of claim 2 further comprising a grasping forceps adapted to be inserted into said cannula at its proximal end, pass through both said loops, and extend beyond the distal end of said cannula.

4. The instrument of claim 3 wherein said forceps has means for marking how far it has been inserted into said cannula.

5. The instrument of claim 2 wherein said transecting material is a fine wire.

6. The instrument of claim 3 further comprising means for displacing said loops beyond the distal end of said cannula.

7. The instrument of claim 1 wherein each said loop is closed by a slip knot, the sutures being connected to their respective loops so as to be capable of tightening the loop via the slip knot in response to pulling on the protruding suture.

8. The instrument of claim 1 further comprising a channel extending lengthwise inside the cannula.

9. The instrument of claim 8 wherein means are provided in said channel through which the sutures can reach the channel from their connections to the respective loops.

10. A method of ligating and transecting comprising the steps of:

positioning a proximal loop and a distal loop axially proximate a distal end of a cannula said cannula having an inner channel and a distal support tube;

placing the cannula in the body of the patient undergoing the ligating and transecting procedure;

inserting a forceps into the inner channel of the cannula so that it extends beyond the distal and grasps an anatomic structure to be ligated and transected;

retracting the forceps with its grasped structure into the cannula past both of said loops;

tightening the distal loop so as to ligate said structure at the location of the distal loop; and tightening the proximal loop so as to transect said structure at the location of the proximal loop.

11. The method of claim 10 wherein the step of tightening the proximal loop also severs the suture passing through said other loop.

12. The method of claim 11 further comprising the step of withdrawing the forceps grasping the transected structure from the cannula, thereby providing "tissue confirmation" and enabling histologic examination of said transected structure.

13. An instrument for use in laparoscopic surgery, comprising:

a generally tubular cannula having a proximal end, a distal end and an axial channel therethrough;

first and second exterior channels located proximate said cannula, said exterior channels being generally parallel to the axial channel of the cannula and being closed at their distal ends, each exterior channel having an aperture proximate their distal ends;

proximal and distal loops closed by manipulating first and second sutures respectively, said loops located in the axial channel proximate the distal end of the cannula, the distal loop located closer to said distal end of the cannula than the proximal loop, wherein the first suture passes through the first exterior channel so that its free end extends from the proximal end of its respective channels, and the second suture passes through said proximal loop and the second exterior channel so that its free end extends from the proximal end of the second exterior channel.

* * * * *

UNITED STATES PATENT AND TRADEMARK OFFICE
CERTIFICATE OF CORRECTION

PATENT NO. : 6,120,513
DATED : September 19, 2000
INVENTOR(S) : Robert W. Bailey and Giles W. Manley It is certified that error appears in the above-identified patent and that said Letters Patent is hereby corrected as shown below:

Claim 10, column 8, line 2 after the word "distal" the words --support tube-- should be inserted.

Signed and Sealed this

Seventeenth Day of April, 2001

Attest:

NICHOLAS P. GODICI

Attesting Officer     *Acting Director of the United States Patent and Trademark Office*